United States Patent
Nelson et al.

(10) Patent No.: US 8,030,525 B2
(45) Date of Patent: Oct. 4, 2011

(54) METHOD FOR PRODUCING PHENOL AND ACETONE

(75) Inventors: Mark E. Nelson, Mount Vernon, IN (US); Arkady Samuilovich Dykman, St. Petersburg (RU); Andrey Vladimirovich Zinenkov, St. Petersburg (RU); Victor Vladimirovich Pinson, St. Petersburg (RU); Ilja Nikolayevich Grebenshchikov, St. Petersburg (RU); Dmitrij Nikolayevich Zhukov, St. Petersburg (RU)

(73) Assignee: Sabic Innovative Plastics IP B.V., Bergen Op Zoom (NL)

( * ) Notice: Subject to any disclaimer, the term of this patent is extended or adjusted under 35 U.S.C. 154(b) by 0 days.

(21) Appl. No.: 12/578,307

(22) Filed: Oct. 13, 2009

(65) Prior Publication Data

US 2010/0099919 A1    Apr. 22, 2010

(30) Foreign Application Priority Data

Oct. 16, 2008  (RU) ................. 2008141213

(51) Int. Cl.
  *C07C 45/00* (2006.01)
  *C07C 37/08* (2006.01)
(52) U.S. Cl. ........................ 568/386; 568/798
(58) Field of Classification Search .............. 568/386, 568/798
  See application file for complete search history.

(56) References Cited

U.S. PATENT DOCUMENTS

| | | | |
|---|---|---|---|
| 3,271,457 A | 9/1966 | Bewley et al. | |
| 4,246,203 A | 1/1981 | Wirth | |
| 6,057,483 A | 5/2000 | Zakoshansky et al. | |
| 7,109,385 B2 | 9/2006 | Tatake et al. | |
| 7,482,493 B2 | 1/2009 | Nelson et al. | |
| 7,485,758 B2 | 2/2009 | Nelson et al. | |
| 2005/0222466 A1 | 10/2005 | Tatake et al. | |

FOREIGN PATENT DOCUMENTS

| | | |
|---|---|---|
| GB | 721700 A | 1/1955 |
| RU | 2068404 C1 | 10/1996 |
| RU | 2121477 C1 | 11/1998 |
| RU | 2291852 C1 | 1/2007 |
| SU | 213892 A1 | 9/1969 |
| WO | 2005/097720 A1 | 10/2005 |

OTHER PUBLICATIONS

Zakoshansky, V.M. Scientific Publication, Conference Materials, Development Prospects for Chemical Processing of Fossil Fuel. "Cumene Process of Phenol-Acetone Production—History and Evolution". Khimizdata, St. Petersburg, RU pp. 25-39, 2006.

(Continued)

*Primary Examiner* — Sikarl Witherspoon
(74) *Attorney, Agent, or Firm* — Michael Best & Friedrich LLP; Todd S. Hofmeister; Paul A. Jenny

(57) ABSTRACT

A method for producing phenol and acetone in a multi-stage process at an elevated temperature from a cumene hydroperoxide mixture comprising cumene, the method comprising the steps of a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage and decomposing the second mixture in a second stage to produce a third mixture comprising phenol and acetone.

15 Claims, 1 Drawing Sheet

2-Stage Cleavage Process Flow

OTHER PUBLICATIONS

Zakoshansky, V.M. "Direction for the Development of Phenolic Process—Safety, Selectivity and Quality of the Products: I. Cumene Oxidation into Cumene Hydroperoxide (CHP)". ISBN 5-901065-94-8. Process of Oil Refining and Petrochemistry. SP6., 2005. pp. 89-107.

Zakoshansky, V.M. "Direction for Phenol Process Development—Security, Selectivity Quality and Marketable Product: II. Decomposition of Technical Cumyl Hydroperioxide". ISBN 5-901065-94-8. Process of Oil Refining and Petrochemistry. SP6., 2005. pp. 108-130.

Vasileva, I.I. and Zakoshansky, V.M. "Direction of Development Phenolic Process—Safety, Selectivity and Quality of the Commodity Products: III. Technologies of Separation and Quality of Products". ISBN 5-901065-94-8. Process of Oil Refining and Petrochemistry. SP6., 2005. pp. 131-154.

Kirk-Othmer Encyclopedia of Chemical Technology. Fourth Edition, vol. 18. Phenol. pp. 592-602, 2001.

Weygand, C. and Hilgetag, I., "Preparative Organic Chemistry", edited by G. Hilgetag and A. Martini. Copyright 1972, By John Wiley & Sons, Inc. pp. 617, 624.

U.S. Appl. No. 12/424,447, filed Apr. 15, 2009, Method for Producing Phenol and Acetone, Mark E. Nelson, et al.

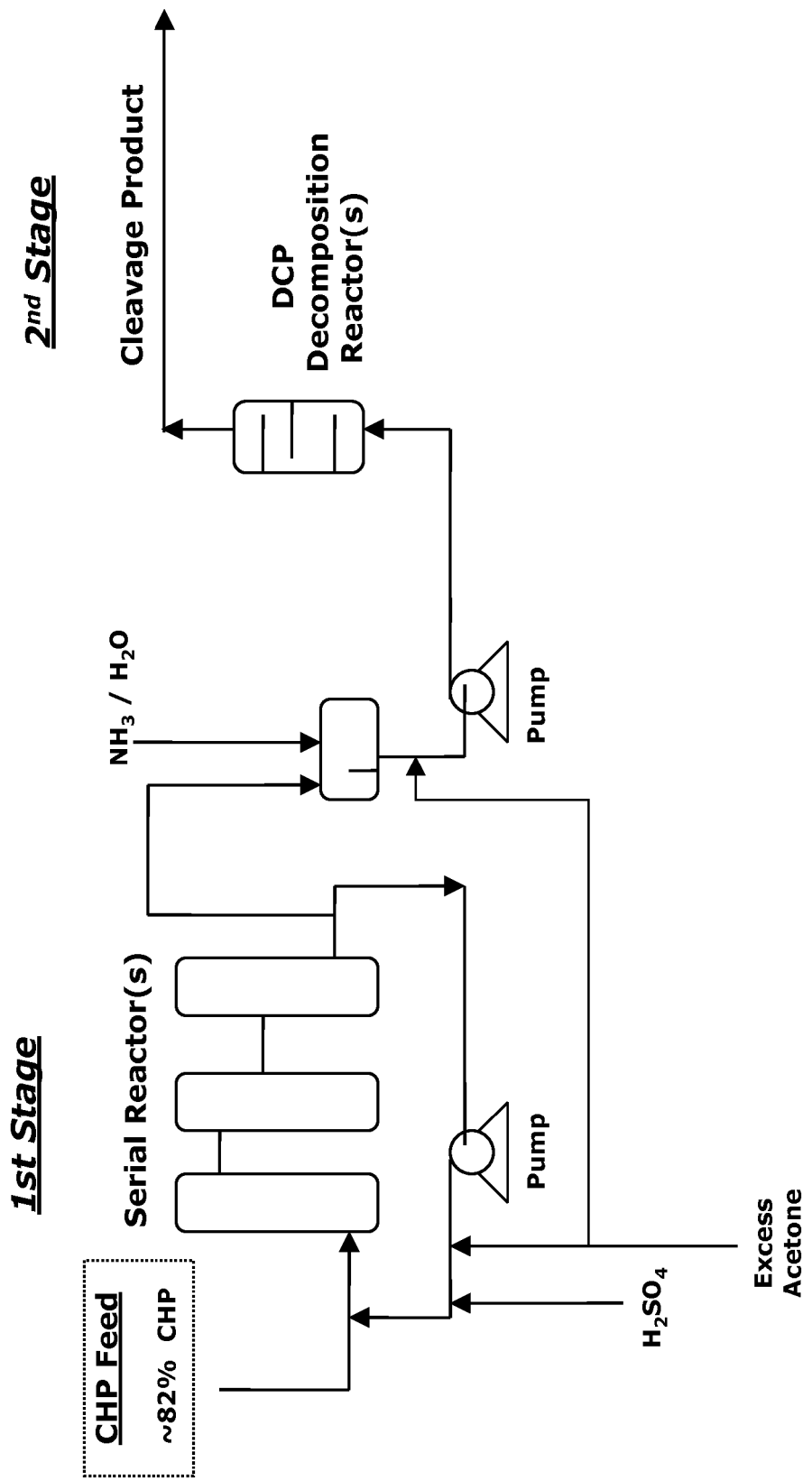
FIGURE – 2-Stage Cleavage Process Flow

METHOD FOR PRODUCING PHENOL AND ACETONE

CROSS REFERENCE TO RELATED APPLICATIONS

This application claims priority to Russian Application Serial No. 2008141213, filed Oct. 16, 2008. This disclosure is hereby fully incorporated herein by reference.

BACKGROUND

The present invention relates to the field of industrial organic synthesis, particularly to the production of phenol and acetone by the cumene method.

A known method for the production of phenol and acetone by the oxidation of cumene with atmospheric oxygen, followed by the acid-catalyzed decomposition of cumene hydroperoxide, makes it possible to obtain both target products (acetone and phenol) at a high yield (Khruzhalov B. D., Golovanenko B. N., Co-production of phenol and acetone, Moscow, GosKhimIzdat, 1964). This method is practiced widely in the production of these products, and is the main method used globally.

Sulfuric acid is used as a catalyst for decomposing cumene hydroperoxide (CHP) at operating plants where phenol and acetone are produced by the cumene method. A method is known for decomposing cumene hydroperoxide by using phenol-2,4-disulfonic acid (also known as 4-hydroxybenzene-1,3-disulfonic acid) (Russian Authors' Certificate No. 213892). The decomposition process is performed in one stage at a catalyst concentration of 0.1 to 0.5 wt % and a temperature of 50° C. This method makes it possible to reduce the formation of phenolic resins (also referred to as "heavies"). However, this reduction is not significant in comparison with the two- to three-fold reduction in the phenolic resin yield levels attained by other known methods, which are further described below.

There are known methods for producing phenol and acetone in which, in order to reduce the yield of phenolic resins, cumene oxidation products containing cumene hydroperoxide (CHP), cumene, and dimethylphenylcarbinol (DMPC, also referred to as dimethylbenzyl alcohol (DMBA)) are cleaved in two stages in the presence of sulfuric acid. The first stage involves decomposition of most (97 to 99%) of CHP and synthesis of dicumyl peroxide (DCP) from DMPC and CHP at 55 to 80° C. The second stage involves adding acetone to the resulting reaction mixture containing phenol, acetone, DMPC, and DCP at a temperature of 80 to 120° C. The acetone is added in an amount equal to 1.5 to 1.8 times its initial concentration. This process is accompanied by the cleavage of the DCP formed in the first stage, decomposition of the residual CHP, and dehydration of the residual DMPC (Russian Patent Nos. 2,068,404 and 2,121,477).

The aforementioned methods for decomposing CHP in two stages make it possible to markedly reduce the amount of byproducts in comparison with the one-stage decomposition (resin yield: 25 kg/t of phenol). At the same time, the amount of the hydroxyacetone (HA) byproduct remains high in these improved two stage processes (for example, more than 1000 ppm).

Hydroxyacetone is a source of 2-methylbenzofuran, which is difficult to separate from phenol and which has an adverse effect on the color indexes of products made from impure commercial-grade phenol. Hydroxyacetone can be removed from phenol, for example, by an alkaline treatment, but this makes the technology of the process more complicated (Vasilieva I. I., Zakoshansky V. M., Collection of articles titled "Petrochemical and Oil Refining Processes," SPb, Giord, 2005, pp. 89-154, 344). Moreover, the existing phenol purification technology requires 1.3 to 2.5 kg/kg of phenol (the molar ratio is from 1:1 to 1:2) to be used in the reaction with hydroxyacetone.

A method is known for decomposing CHP in two stages (Russian Patent No 2,142,932, U.S. Pat. No. 6,057,483). This CHP decomposition process is carried out in three serially arranged mixing reactors in the first stage, and a displacement reactor in the second stage. The CHP is decomposed in the first stage under conditions close to isothermal (that is, at a temperature of 47 to 50° C. and a concentration of 0.018 to 0.020 mass % for the sulfuric acid catalyst), while the reaction mass is additionally diluted with acetone in an amount equal to 5 to 8 mass % relative to the amount of supplied CHP. Almost all of the CHP reacts in the process, and DCP forms from part of CHP and DMPC.

The process in the second stage is carried out while the sulfuric acid is partially neutralized with ammonia, forming ammonium hydrosulfate at a temperature of 120 to 140° C., and while some water is added. The concentration of sulfuric acid is 0.009 to 0.010 mass %. The CHP and DCP are decomposed in a reaction medium containing phenol and acetone, both of which are formed from the CHP. Additional acetone may optionally be added to the reactor if desired.

A method is known for decomposing technical-grade CHP in serially connected reactors in two stages so that the CHP is partially decomposed and dicumyl peroxide is formed in the first stage at a temperature of 40 to 65° C. in the presence of 0.003 to 0.015 mass % of sulfuric acid as a catalyst, followed by the decomposition of CHP and DCP in the second stage at a temperature of 90 to 140° C. The process is performed using excess phenol in the reaction medium at a phenol/acetone molar ratio greater than 1, and preferably from 1.01 to 5. The excess phenol is produced either by driving off acetone or by adding phenol to the reaction medium (see, for example, Russian Patent No. 2,291,852). When technical-grade CHP is decomposed under these conditions, the hydroxyacetone yield is reduced to 0.04 mass % (400 parts per million (ppm)) in the reaction medium, whereby the quality of the commercial-grade phenol is markedly improved. However, application of this method is premised on the use of phenol that has been purified in a phenol purification system, and the purification of phenol involves additional manufacturing steps and power consumption.

Some disadvantages of the prior art methods are the presence of hydroxyacetone (HA) in the resulting phenol, and in some cases the need for quenching excess sulfuric acid during the second stage. The presence of HA has an adverse effect on the phenol quality while the quenching of sulfuric acid results in additional complexity and processing steps as well as higher operating costs in the process. Therefore, there is a need for a method to further reduce the amount of HA in the phenol produced and to eliminate entirely the sulfuric acid quenching step or at least substantially reduce the amount of neutralization agent required in the quenching step.

SUMMARY OF THE INVENTION

Some or all of the above-described deficiencies are addressed by a method for producing phenol and acetone in a multi-stage process at an elevated temperature from a cumene hydroperoxide mixture comprising cumene, the method for producing phenol and acetone in a multi-stage process at an elevated temperature from a cumene hydroperoxide mixture comprising cumene, the method comprising the steps of a)

reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is of the general formula:

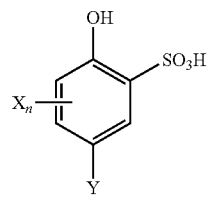

wherein each X is independently alkyl, aralkyl, halogen, hydroxyalkyl, sulfonic acid, combinations thereof, or substituents thereof, Y is hydrogen, alkyl, aralkyl, halogen, hydroxyalkyl, sulfonic acid, combinations thereof, or substituents thereof and n is 0 to 3, and b) decomposing the second mixture in a second stage to produce a third mixture comprising phenol and acetone.

In another embodiment, a method for producing phenol and acetone in a multi-stage process at an elevated temperature from a cumene hydroperoxide mixture comprising cumene is disclosed, the method comprising the steps of: a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is of the general formula:

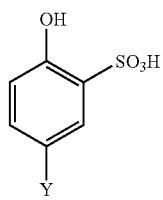

wherein each Y is hydrogen, alkyl, aralkyl, halogen, hydroxyalkyl, sulfonic acid, combinations thereof, or substituents thereof and n is 0 to 3, and b) decomposing the second mixture in a second stage to produce a third mixture comprising phenol and acetone.

In another embodiment, a method for producing phenol and acetone in a multi-stage process at an elevated temperature from a cumene hydroperoxide mixture comprising cumene is disclosed, the method comprising the steps of: a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is selected from the group consisting of 2-hydroxy-5-cumylbenzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid and 2-hydroxy-5-methylbenzenesulfonic acid, and b) decomposing the second mixture in a second stage to produce a third mixture comprising phenol and acetone.

BRIEF DESCRIPTION OF THE DRAWING

The FIGURE is a process flow diagram of an embodiment of the two-stage cleavage process of the invention.

DETAILED DESCRIPTION OF THE INVENTION

The inventors have found a way to further reduce the amount of hydroxyacetone (HA) in the decomposition products (phenol and acetone) of technical-grade CHP while also increasing capacity by decomposing the technical-grade CHP in the presence of a specific type of catalyst. Disclosed herein is a method for producing phenol and acetone in a multi-stage process at an elevated temperature from a cumene hydroperoxide mixture comprising cumene, the method for producing phenol and acetone in a multi-stage process at an elevated temperature from a cumene hydroperoxide mixture comprising cumene, the method comprising the steps of a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is of the general formula:

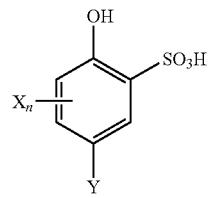

wherein each X is independently alkyl, aralkyl, halogen, hydroxyalkyl, sulfonic acid, combinations thereof, or substituents thereof, Y is hydrogen, alkyl, aralkyl, halogen, hydroxyalkyl, sulfonic acid, combinations thereof, or substituents thereof and n is 0 to 3, and b) decomposing the second mixture in a second stage to produce a third mixture comprising phenol and acetone.

In another embodiment, a method for producing phenol and acetone in a multi-stage process at an elevated temperature from a cumene hydroperoxide mixture comprising cumene is disclosed, the method comprising the steps of: a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is of the general formula:

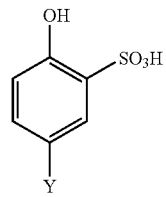

wherein each Y is hydrogen, alkyl, aralkyl, halogen, hydroxyalkyl, sulfonic acid, combinations thereof, or substituents thereof and n is 0 to 3, and b) decomposing the second mixture in a second stage to produce a third mixture comprising phenol and acetone.

In another embodiment, a method for producing phenol and acetone in a multi-stage process at an elevated temperature from a cumene hydroperoxide mixture comprising cumene is disclosed, the method comprising the steps of: a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is selected from the group consisting of 2-hydroxy-5-cumyl-benzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid and 2-hydroxy-5-methylbenzenesulfonic acid, and b) decomposing the second mixture in a second stage to produce a third mixture comprising phenol and acetone.

The catalyst is a substituted 2-hydroxybenzenesulfonic acid of the general formula:

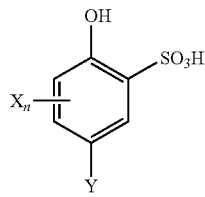

wherein each X is independently hydrogen, alkyl, aralkyl, halogen, hydroxyalkyl, sulfonic acid, combinations thereof, or substituents thereof, Y is hydrogen, alkyl, aralkyl, halogen, hydroxyalkyl, sulfonic acid, combinations thereof, or substituents thereof, and n is 0 to 3. As used herein, "sulfonic acid" is defined as a sulfo group, which may also be expressed as $SO_3H$ or $SO_2OH$, and the terms may be used interchangeably throughout. In an embodiment, n is) and Y is not hydrogen (i.e., Y is alkyl, aralkyl, halogen, hydroxyalkyl, sulfonic acid, combinations thereof, or substituents thereof).

In an embodiment, the catalyst is a substituted 2-hydroxybenzenesulfonic acid of the general formula:

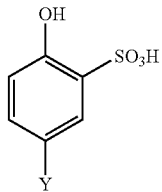

wherein Y is hydrogen, alkyl, aralkyl, halogen, hydroxyalkyl, sulfonic acid, combinations thereof, or substituents thereof. In an embodiment, Y is not hydrogen.

In an embodiment, Y is hydrogen, $C_1$ to $C_{18}$ alkyl, $C_6$ to $C_{18}$ aralkyl, halogen, $C_1$ to $C_{18}$ hydroxyalkyl, sulfonic acid, combinations thereof, or substituents thereof. The substituted 2-hydroxybenzenesulfonic acid has at least one hydroxyl group and one sulfonic acid group in neighboring positions on the aromatic ring, although there may be additional neighboring hydroxyl and sulfonic acid groups present. In an embodiment, Y is not hydrogen. This structure, having at least one hydroxyl group and one sulfonic acid group in neighboring positions on the aromatic ring is advantageous in the CHP cleavage process.

Examples of substituted 2-hydroxybenzenesulfonic acids that can be used as catalysts include, but are not limited to, 2-hydroxy-5-chlorobenzenesulfonic acid (where n is 0, Y is Cl), 2-hydroxy-5-cumyl-benzenesulfonic acid (where n is 0, Y is 1-methyl-1-phenylethyl), 4-hydroxybenzene-1,3-disulfonic acid (where n is 0 and Y is $SO_3H$), 3,3'-propane-2,2-diyl-bis-(6-hydroxybenzenesulfonic) acid (two pairs of sulfonic acid and hydroxyl groups per catalyst molecule), 2-hydroxy-5-methoxybenzenesulfonic acid (where n is 0, Y is $OCH_3$), 2-hydroxy-5-methylbenzenesulfonic acid (where n is 0, Y is $CH_3$), 2-hydroxy-4-t-butyl-benzenesulfonic acid (where n is 0 and Y is tert-butyl) and 2-hydroxybenzenesulfonic acid (where n is 0, Y is H).

In embodiments, the 2-hydroxybenzenesulfonic acid catalyst is selected from the group consisting of 2-hydroxy-5-cumyl-benzenesulfonic acid, 4-hydroxybenzene-1,3-disulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid, 2-hydroxy-5-methylbenzenesulfonic acid, 2-hydroxy-4-t-butyl-benzenesulfonic acid and 2-hydroxybenzenesulfonic acid, specifically 2-hydroxy-5-cumyl-benzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid, 2-hydroxy-5-methylbenzenesulfonic acid, 2-hydroxy-4-t-butyl-benzenesulfonic acid and 2-hydroxybenzenesulfonic acid.

In an embodiment, the reacting in the first stage is at a temperature of from 40 to 75° C. In an embodiment, the decomposing in the second stage is at a temperature of from 110 to 140° C. In an embodiment, the reacting in the first stage is at a temperature of from 40 to 75° C. and the decomposing in the second stage is at a temperature of from 110 to 140° C.

As used herein, technical-grade cumene hydroperoxide (CHP) refers to CHP having a CHP concentration of from about 50 to 92 mass %, specifically from about 65 to 85 mass %, more specifically from 80 to 84 mass %. The actual CHP concentration is not critical, but in an embodiment, the CHP concentration is at least 50 mass %.

The substituted 2-hydroxybenzenesulfonic acids can be obtained by a known method, for example, by the treatment of the corresponding phenol with an equimolar amount of chlorosulfonic acid in dichloromethane or a similar solvent (see, for example, Weigand and Hilgetag, Experimental Methods in Organic Chemistry, Translated from German; edited by Prof. N. N. Suvorov, Moscow, Khimiya Publishers, 1968, or Weygand-Hilgetag, Organish-Chemische Experimentierkunst, Johann Ambrosius Barth Verlag, Leigzig, 1964). Sulfonation of a phenol to form a 2-hydroxybenzenesulfonic acid is accomplished in higher yields when the 4-position of the phenol is blocked by a substituent group at the 4-position. It was also found that the 4-hydroxybenzenesulfonic acids were less effective than the 2-hydroxybenzenesulfonic acids in the CHP decomposition process.

The process for decomposing technical-grade CHP and forming phenol and acetone by using the aforementioned acids is performed in multiple stages, such as at least two serially connected reactors. In an embodiment, the step of reacting the cumene hydroperoxide is in at least two serially connected reactors. In the first stage, CHP is decomposed at a temperature of 40 to 75° C. and an acid catalyst concentration of 0.1 to 1 mmol/L while the reaction mass is circulated. The acid catalyst concentration depends on several factors, such as the temperature in the reactors, the phenol/acetone ratio, and the water and DMPC content of the raw material (technical-grade CHP); that is, the required catalyst concentration increases with increased concentration of water and DMPC in the raw material and with reduced phenol/acetone ratio. The feed rate of the raw material CHP (the volume of CHP fed) must not exceed 10% (in embodiments, less than 5%) of the volume of the circulating reaction mass while the circulation factor (the ratio of the flow rate of the circulating mass to the flow rate of the raw material being fed) is kept above 9. Under these conditions, CHP decomposes to form phenol and acetone, and DCP is synthesized from CHP and DMPC, at a CHP conversion rate of 95 to 99.8%. The synthesized DCP and the residual CHP are decomposed in the second stage at a temperature of 110 to 140° C. The heat released during CHP decomposition is removed by heat exchangers in order to maintain a set temperature in the reactors. In embodiments, the heat exchangers are built into the reactors.

By using a substituted 2-hydroxybenzenesulfonic acid, the hydroxyacetone yield decreases by 1.5 to 3 times (concentration of CHP in the decomposition reaction mass: 0.03 to 0.09%) under the aforementioned conditions, a technical-grade CHP composition that is similar to the conventional composition can be used in the process and the quality of the commercial-grade phenol can be improved without the need to use excess phenol (see, for example, application Ser. No. 12/424,447, filed Apr. 15, 2009, for an example of a process using excess phenol to improve quality). In an embodiment, the third mixture has a hydroxyacetone concentration of less than 0.10 mass %, specifically less than 0.05 mass %, based on the total mass % of the third mixture. Moreover, the high catalytic activity of the proposed substituted 2-hydroxybenzenesulfonic acids makes it possible to reduce the molar amount of the acid used, whereby the consumption of a base such as sodium hydroxide or ammonia that is used to neutralize the acid after cleavage is reduced, thus reducing the amount of the neutralized salt waste generated in the production process. Advantageously, the use of lower molar amounts of acid allows for the elimination of the alkali neutralization step under some circumstances, thus further simplifying the process and reducing costs. In an embodiment, the second mixture is not quenched with an alkaline material prior to step b).

The method is illustrated by the following non-limiting examples.

EXAMPLES

Example 1

Cumene hydroperoxide is decomposed using a pilot plant comprising two reactors: a first-stage CHP decomposition reactor that has a volume of 12 mL and is provided with a circulation loop, and a second-stage reactor that has a volume of 7 mL and is a displacement reactor. Part of the reaction mass from the first-stage reactor is fed to the second-stage reactor, and part of the mass is returned to the inlet of the first-stage reactor, and is thereby circulated. A catalyst and a raw material are fed to the reaction mass stream at the inlet to the first-stage reactor. The composition of the raw material is shown in Table 1.

TABLE 1

Raw material used for the decomposition of CHP

| | Component | Content, mass % |
|---|---|---|
| 1 | Cumene hydroperoxide (CHP) | 74.55 |
| 2 | Cumene | 14.22 |

TABLE 1-continued

Raw material used for the decomposition of CHP

| | Component | Content, mass % |
|---|---|---|
| 3 | Dimethylphenylcarbinol (DMPC) | 2.61 |
| 4 | Acetophenone | 0.32 |
| 5 | Water | 0.71 |
| 6 | Dicumyl peroxide (DCP) | 0.21 |
| 7 | Phenol | 0.76 |
| 8 | Acetone | 6.37 |
| 9 | Unidentified | 0.25 |

The CHP decomposition reactor was charged with the technical-grade CHP having the composition shown in Table 1 at a rate of 30 mL/hour. The catalyst fed into the reactor was a freshly prepared solution of 2-hydroxy-5-chlorobenzenesulfonic acid (n is 0, Y is Cl) having a concentration of 0.32 mol/L. The catalyst solution was fed at a rate of 50 μL/hour. The concentration of 2-hydroxy-5-chlorobenzenesulfonic acid in the reactor in a stationary state was 0.5 mmol/L (0.013% or 130 ppm). The circulation rate of the reaction mass was 500 mL/hour. The temperature in the reactor was maintained at a level of 50° C. by supplying a heat-transfer medium having an appropriate temperature into the reactor jacket.

The stream leaving the first-stage reactor was diluted with acetone, which was fed at a rate of 8 mL/hour to the second-stage reactor, which was heated to 125° C. The stream leaving the second-stage reactor was cooled and analyzed by gas-liquid chromatography. The composition of the CHP decomposition reaction mass after leaving the second stage reactor is shown in Table 2.

TABLE 2

Composition of CHP decomposition reaction mass

| Component | Concentration, mass % |
|---|---|
| Phenol | 39.9 |
| Acetone | 43.97 |
| Dicumyl peroxide (DCP) | 0.02 |
| Dimethylphenylcarbinol (DMPC) | 0.04 |
| Cumylphenols | 0.24 |
| Total of α-methylstyrene dimers | 0.08 |
| Acetophenone | 0.46 |
| α-Methylstyrene (AMS) | 1.48 |
| Cumene | 11.97 |
| Hydroxyacetone | 0.04 |
| Mesityl oxide | 0.01 |
| Unidentified | 0.42 |
| Water | 1.37 |

Example 2

CHP was decomposed using the same equipment and under the same conditions as in Example 1, except that a freshly prepared solution of 2-hydroxy-5-cumyl-benzenesulfonic acid (where n is 0, Y is 1-methyl-1-phenylethyl) having a concentration of 0.32 mol/L was used as a catalyst. The catalyst solution was fed at a rate of 50 μL/hour, whereby a concentration of 0.5 mmol/L (0.015% or 150 ppm) was maintained in the reaction mass. The composition of the CHP decomposition reaction mass after leaving the second stage reactor is shown in Table 3.

TABLE 3

Composition of CHP decomposition reaction mass

| Component | Concentration, mass % |
|---|---|
| Phenol | 40.4 |
| Acetone | 43.73 |
| Dicumyl peroxide (DCP) | 0.02 |
| Dimethylphenylcarbinol (DMPC) | 0.04 |
| Cumylphenols | 0.24 |
| Total of α-methylstyrene dimers | 0.07 |
| Acetophenone | 0.46 |
| α-Methylstyrene (AMS) | 1.44 |
| Cumene | 11.73 |
| Hydroxyacetone | 0.03 |
| Mesityl oxide | 0.01 |
| Unidentified | 0.44 |
| Water | 1.39 |

Example 3

CHP was decomposed using the same equipment and under the same conditions as in Example 1, except that the temperature in the first stage was 40° C., and a freshly prepared solution of 4-hydroxybenzene-1,3-disulfonic acid (where n is 0 and Y is $SO_3H$) having a concentration of 0.32 mol/L was used as a catalyst. The catalyst solution was fed at a rate of 100 μL/hour (1 mmol/L (0.025% or 250 ppm) in the reaction mass). The composition of the CHP decomposition reaction mass after leaving the second stage reactor is shown in Table 4.

TABLE 4

The composition of the CHP decomposition reaction mass

| Component | Concentration, mass % |
|---|---|
| Phenol | 39.43 |
| Acetone | 43.9 |
| Dicumyl peroxide (DCP) | 0.02 |
| Dimethylphenylcarbinol (DMPC) | 0.07 |
| Cumylphenols | 0.34 |
| Total of α-methylstyrene dimers | 0.19 |
| Acetophenone | 0.46 |
| α-Methylstyrene (AMS) | 1.39 |
| Cumene | 11.81 |
| Hydroxyacetone | 0.09 |
| Mesityl oxide | 0.02 |
| Unidentified | 0.67 |
| Water | 1.61 |

Example 4

CHP was decomposed using the same equipment and under the same conditions as in Example 1, except that a freshly prepared solution of 3,3'-propane-2,2-diyl-bis-(6-hydroxybenzenesulfonic) acid (two pairs of sulfonic acid and hydroxyl groups per catalyst molecule, having the structure below) having a concentration of 0.32 mol/L was used as a catalyst.

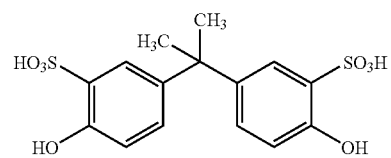

3,3'-propane-2,2-diyl-bis-(6-hydroxybenzenesulfonic) acid

The catalyst solution was fed at a rate 50 μL/hour (0.5 mmol/L (0.021% or 210 ppm) in the reaction mass). The composition of the CHP decomposition reaction mass after leaving the second stage reactor is shown in Table 5.

TABLE 5

Composition of CHP decomposition reaction mass

| Component | Concentration, mass % |
|---|---|
| Phenol | 39.77 |
| Acetone | 43.68 |
| Dicumyl peroxide (DCP) | 0.04 |
| Dimethylphenylcarbinol (DMPC) | 0.08 |
| Cumylphenols | 0.41 |
| Total of α-methylstyrene dimers | 0.36 |
| Acetophenone | 0.47 |
| α-Methylstyrene (AMS) | 1.82 |
| Cumene | 11.38 |
| Hydroxyacetone | 0.08 |
| Mesityl oxide | 0.01 |
| Unidentified | 0.60 |
| Water | 1.29 |

Example 5

CHP was decomposed using the same equipment and under the same conditions as in Example 1, except that the raw material did not contain any additionally introduced acetone and that water was added to the initial technical-grade CHP raw material (having the composition shown in Table 6) in an amount of up to 0.5%. The acetone was fed to the two stages at a rate of 11 mL/hour.

TABLE 6

Raw material used for CHP decomposition

| | Component | Content, mass % |
|---|---|---|
| 1 | Cumene hydroperoxide (CHP) | 80.15 |
| 2 | Cumene | 11.81 |
| 3 | Dimethylphenylcarbinol (DMPC) | 5.82 |
| 4 | Acetophenone | 0.93 |
| 5 | Water | 0.49 |
| 6 | Dicumyl peroxide (DCP) | 0.32 |
| 7 | Phenol | 0.04 |
| 8 | Unidentified | 0.44 |

A freshly prepared solution of 2-hydroxy-5-methoxybenzenesulfonic acid (where n is 0, Y is $OCH_3$) having a concentration of 0.32 mol/L was used as a catalyst. The catalyst solution was fed at a rate of 28 μL/hour (0.3 mmol/L (0.006% or 60 ppm) in the reaction mass). The composition of the CHP decomposition reaction mass after leaving the second stage reactor is shown in Table 7.

TABLE 7

Composition of CHP decomposition reaction mass

| Component | Concentration, mass % |
|---|---|
| Phenol | 39.76 |
| Acetone | 44.86 |
| Dicumyl peroxide (DCP) | 0.05 |
| Dimethylphenylcarbinol (DMPC) | 0.11 |
| Cumylphenols | 0.09 |
| Total of α-methylstyrene dimers | 0.14 |
| Acetophenone | 0.95 |
| α-Methylstyrene (AMS) | 3.03 |
| Cumene | 8.69 |
| Hydroxyacetone | <0.03 |
| Mesityl oxide | 0.004 |
| Unidentified | 0.59 |
| Water | 1.7 |

Example 6

CHP was decomposed using the same equipment as in Example 1, except that the second stage of the process was conducted at a temperature of 110° C. A freshly prepared solution of 2-hydroxy-5-methylbenzenesulfonic acid (where n is 0, Y is $CH_3$) having a concentration of 0.32 mol/L was used as a catalyst. The catalyst solution was fed at a rate of 28 μL/hour (0.3 mmol/L (0.006% or 60 ppm) in the reaction mass). The composition of the CHP decomposition reaction mass after leaving the second stage reactor is shown in Table 8.

TABLE 8

Composition of CHP decomposition reaction mass

| Component | Concentration, mass % |
|---|---|
| Phenol | 39.73 |
| Acetone | 43.89 |
| Dicumyl peroxide (DCP) | 1.16 |
| Dimethylphenylcarbinol (DMPC) | 0.35 |
| Cumylphenols | 0.23 |
| Total of α-methylstyrene dimers | 0.11 |
| Acetophenone | 0.94 |
| α-Methylstyrene (AMS) | 2.42 |
| Cumene | 8.86 |
| Hydroxyacetone | <0.03 |
| Mesityl oxide | 0.01 |
| Unidentified | 0.52 |
| Water | 1.78 |

Example 7

CHP was decomposed using the same equipment as in Example 1, except that the first stage of the process was conducted at 75° C., and the second-stage of the process was conducted at a temperature of 140° C. A freshly prepared solution of 2-hydroxy-5-cumyl-benzenesulfonic acid having a concentration of 0.32 mol/L was used as a catalyst. The catalyst solution was fed at a rate of 12 μL/hour (0.1 mmol/L (0.004% or 40 ppm) in the reaction mass). The composition of the CHP decomposition reaction mass after leaving the second stage reactor is shown in Table 9.

TABLE 9

Composition of CHP decomposition reaction mass

| Component | Concentration, mass % |
|---|---|
| Phenol | 39.74 |
| Acetone | 44.65 |
| Dicumyl peroxide (DCP) | 0.007 |
| Dimethylphenylcarbinol (DMPC) | 0.09 |
| Cumylphenols | 0.12 |
| Total of α-methylstyrene dimers | 0.14 |
| Acetophenone | 1.12 |
| α-Methylstyrene (AMS) | 3.03 |
| Cumene | 8.75 |
| Hydroxyacetone | <0.03 |
| Mesityl oxide | 0.007 |
| Unidentified | 0.54 |
| Water | 1.81 |

Example 8 (Comparative Example)

CHP was decomposed using the same equipment as in Example 1, except that the conditions of cumene hydroperoxide cleavage were as follows: the first stage of the process was conducted at 50° C., and the second stage of the process was conducted at a temperature of 140° C. (corresponding to the conditions in U.S. Pat. No. 6,057,483). Sulfuric acid having a concentration of 94% was used as a catalyst. The catalyst solution was fed at a rate of 3 μL/hour (0.018% or 180 ppm in the reaction mass). The reaction mixture exiting the first cleavage stage was additionally diluted with acetone fed at 8 ml/hr rate and was partially neutralized (about 50%) by a 2.5% water solution of $NH_3$ providing the concentration of sulfuric acid in the second cleavage stage reactor of 0.009% (90 ppm). The temperature of the second stage cleavage reactor was maintained at 135° C. The composition of CHP decomposition reaction mass after leaving the second stage reactor is shown in Table 10.

TABLE 10

Composition of CHP decomposition reaction mass

| Component | Concentration, mass % |
|---|---|
| Phenol | 40.09 |
| Acetone | 43.74 |
| Dicumyl peroxide (DCP) | 0.01 |
| Dimethylphenylcarbinol (DMPC) | 0.04 |
| Cumylphenols | 0.20 |
| Total of α-methylstyrene dimers | 0.09 |
| Acetophenone | 0.48 |
| α-Methylstyrene (AMS) | 1.51 |
| Cumene | 11.79 |
| Hydroxyacetone | 0.14 |
| Mesityl oxide | 0.01 |
| Unidentified | 0.46 |
| Water | 1.44 |

TABLE 11

Concentration of HA in decomposition reaction mass

| Example | Concentration, mass % |
|---|---|
| Example 1 | 0.04 |
| Example 2 | 0.03 |
| Example 3 | 0.09 |
| Example 4 | 0.08 |
| Example 5 | <0.03 |
| Example 6 | <0.03 |

TABLE 11-continued

| Concentration of HA in decomposition reaction mass | |
| --- | --- |
| Example | Concentration, mass % |
| Example 7 | <0.03 |
| Example 8 (Comparative) | 0.14 |

Table 11 is a summary of the final concentration of hydroxyacetone (HA) in the reaction mass after leaving the second stage reactor for all the Examples. When a 2-hydroxybenzenesulfonic acid catalyst is used, the amount of HA is less than 0.10 mass % (as shown in Examples 1 to 7), and in some cases, less than 0.05 mass %, while when a conventional catalyst, such as sulfuric acid, is used, the amount of HA in the CHP decomposition mass is higher, and in some cases, more than four times higher, than the Examples (0.14, as shown in the Comparative Example).

In Examples 2 and 7, the same 2-hydroxybenzenesulfonic acid catalyst (2-hydroxy-5-cumyl-benzenesulfonic acid) was used, but the reactions were run at different temperatures. At the higher temperatures of Example 7, the amount of HA in the CHP decomposition mass is reduced even further.

The invention claimed is:

1. A method for producing phenol and acetone in a multi-stage process at an elevated temperature from a cumene hydroperoxide mixture comprising cumene, the method comprising the steps of:
    (a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first state, wherein the 2-hydroxybenzenesulfonic acid catalyst is selected from the group consisting of 2-hydroxy-5-cumyl-benzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid, 2-hydroxy-5-methylbenzenesulfonic acid, 2-hydroxy-4-t-butyl-benzenesulfonic acid and 2-hydroxybenzenesulfonic acid, and
    (b) decomposing the second mixture in a second stage to produce a third mixture comprising phenol and acetone.

2. The method of claim 1, wherein the reacting in the first stage is at a temperature of from 40 to 75° C., and the decomposing in the second state is at a temperature of from 110 to 140° C.

3. The method of claim 1, wherein the step of reacting the cumene hydroperoxide is in at least two serially connected reactors.

4. The method of claim 1, wherein the cumene hydroperoxide concentration is from about 50 to 92 mass %.

5. The method of claim 1, wherein the cumene hydroperoxide concentration is from about 80 to 84 mass %.

6. The method of claim 1, wherein the second mixture is not quenched with an alkaline material prior to step b).

7. The method of claim 1, wherein the third mixture has a hydroxyacetone concentration of less than 0.10 mass %, based on the total mass % of the third mixture.

8. The method of claim 1, wherein the third mixture has a hydroxyacetone concentration of less than 0.05 mass %, based on the total mass % of the third mixture.

9. A method for producing phenol and acetone in a multi-stage process at an elevated temperature from a cumene hydroperoxide mixture comprising cumene, the method comprising the steps of:
    (a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is selected from the group consisting of 2-hydroxy-5-cumyl-benzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid, 2-hydroxy-5-methylbenzenesulfonic acid and 2-hydroxybenzenesulfonic acid, and
    (b) decomposing the second mixture in a second stage to produce a third mixture comprising phenol and acetone.

10. The method of claim 9, wherein the third mixture has a hydroxyacetone concentration of less than 0.10 mass %, based on the total mass % of the third mixture.

11. The method of claim 9, wherein the second mixture is not quenched with an alkaline material prior to step b).

12. A method for producing phenol and acetone in a multi-stage process at an elevated temperature from a cumene hydroperoxide mixture comprising cumene, the method comprising the steps of:
    (a) reacting the cumene hydroperoxide mixture with a 2-hydroxybenzenesulfonic acid catalyst having a concentration of 0.1 to 1 mmol/L acid catalyst to form a second mixture comprising phenol, acetone and dicumyl peroxide in a first stage, wherein the 2-hydroxybenzenesulfonic acid catalyst is selected from the group consisting of 2-hydroxy-5-cumyl-benzenesulfonic acid, 3,3'-propane-2,2-diyl-bis-(6-hydroxybenzenesulfonic) acid, 2-hydroxy-5-chlorobenzenesulfonic acid, 2-hydroxy-5-methoxybenzenesulfonic acid and 2-hydroxy-5-methylbenzenesulfonic acid, and
    (b) decomposing the second mixture in a second stage to produce a third mixture comprising phenol and acetone.

13. The method of claim 12, wherein the third mixture has a hydroxyacetone concentration of less than 0.10 mass %, based on the total mass % of the third mixture.

14. The method of claim 12, wherein the third mixture has a hydroxyacetone concentration of less than 0.05 mass %, based on the total mass % of the third mixture.

15. The method of claim 12, wherein the second mixture is not quenched with an alkaline material prior to step b).

* * * * *